United States Patent
Suzuki

(10) Patent No.: US 10,863,963 B2
(45) Date of Patent: Dec. 15, 2020

(54) RADIATION IMAGING APPARATUS, TRANSFER CONTROL METHOD, AND STORAGE MEDIUM

(71) Applicant: CANON KABUSHIKI KAISHA, Tokyo (JP)

(72) Inventor: Tatsuya Suzuki, Tokyo (JP)

(73) Assignee: Canon Kabushiki Kaisha, Tokyo (JP)

(*) Notice: Subject to any disclaimer, the term of this patent is extended or adjusted under 35 U.S.C. 154(b) by 27 days.

(21) Appl. No.: 16/245,531

(22) Filed: Jan. 11, 2019

(65) Prior Publication Data

US 2019/0223825 A1    Jul. 25, 2019

(30) Foreign Application Priority Data

Jan. 19, 2018 (JP) .................... 2018-007249

(51) Int. Cl.
*A61B 6/00* (2006.01)
*G06T 7/00* (2017.01)

(52) U.S. Cl.
CPC .............. *A61B 6/563* (2013.01); *A61B 6/465* (2013.01); *A61B 6/487* (2013.01); *A61B 6/548* (2013.01); *G06T 7/0012* (2013.01); *G06T 2207/10121* (2013.01); *G06T 2207/30004* (2013.01)

(58) Field of Classification Search
CPC ......... A61B 6/563; A61B 6/465; A61B 6/487; A61B 6/548; G06T 7/0012; G06T 2207/10121; G06T 2207/30004
See application file for complete search history.

(56) References Cited

U.S. PATENT DOCUMENTS

| | | | | |
|---|---|---|---|---|
| 5,612,985 A | * | 3/1997 | Toki | A61B 5/0456 378/20 |
| 7,006,678 B2 | * | 2/2006 | Sawada | A61B 6/00 382/132 |
| 9,198,271 B2 | * | 11/2015 | Miyachi | H05G 1/60 |
| 2005/0088566 A1 | * | 4/2005 | Tamura | H04N 5/367 348/362 |
| 2007/0009088 A1 | * | 1/2007 | Edic | G01N 23/046 378/62 |
| 2009/0201841 A1 | * | 8/2009 | Tachikawa | H04L 12/413 370/310 |
| 2011/0280374 A1 | * | 11/2011 | Ohta | G01T 1/243 378/114 |
| 2013/0168558 A1 | * | 7/2013 | Tsuchiya | A61B 6/54 250/363.01 |
| 2013/0170617 A1 | * | 7/2013 | Tsuchiya | G01N 23/04 378/62 |

(Continued)

FOREIGN PATENT DOCUMENTS

| JP | 2002-140687 A | | 5/2002 |
|---|---|---|---|
| JP | 2013-34621 A | | 2/2013 |
| JP | 2013034621 A | * | 2/2013 |

*Primary Examiner* — Taeho Jo
(74) *Attorney, Agent, or Firm* — Canon U.S.A., Inc. IP Division

(57) ABSTRACT

A radiation imaging apparatus that transfers captured images to an external apparatus without lowering operability includes an acquisition unit that acquires a radiation image, and a transfer control unit that transfers the radiation image to a first external apparatus in the case where an elapsed time from a point in time when the radiation image is acquired exceeds a first time.

7 Claims, 6 Drawing Sheets

(56) References Cited

U.S. PATENT DOCUMENTS

| | | | | |
|---|---|---|---|---|
| 2013/0230141 | A1* | 9/2013 | Miyachi | G01N 23/04 378/62 |
| 2014/0233704 | A1* | 8/2014 | Nishii | A61B 6/464 378/98 |
| 2014/0239188 | A1* | 8/2014 | Tezuka | A61B 6/4233 250/394 |
| 2014/0254765 | A1* | 9/2014 | Asai | A61B 6/5258 378/98.5 |
| 2015/0078522 | A1* | 3/2015 | Makino | A61B 6/4405 378/62 |
| 2015/0378030 | A1* | 12/2015 | Tamura | H04N 5/32 378/98.2 |
| 2016/0029986 | A1* | 2/2016 | Nishii | A61B 6/4233 250/394 |
| 2016/0143602 | A1* | 5/2016 | Hiroike | A61B 6/463 378/98.5 |
| 2016/0220211 | A1* | 8/2016 | Yamada | A61B 6/4208 |
| 2017/0163869 | A1* | 6/2017 | Semba | G16H 30/20 |
| 2017/0224290 | A1* | 8/2017 | Ishioka | A61B 6/4233 |
| 2017/0332987 | A1* | 11/2017 | Nonaka | A61B 6/5258 |
| 2018/0135975 | A1* | 5/2018 | Ohyama | G01B 11/2527 |

* cited by examiner

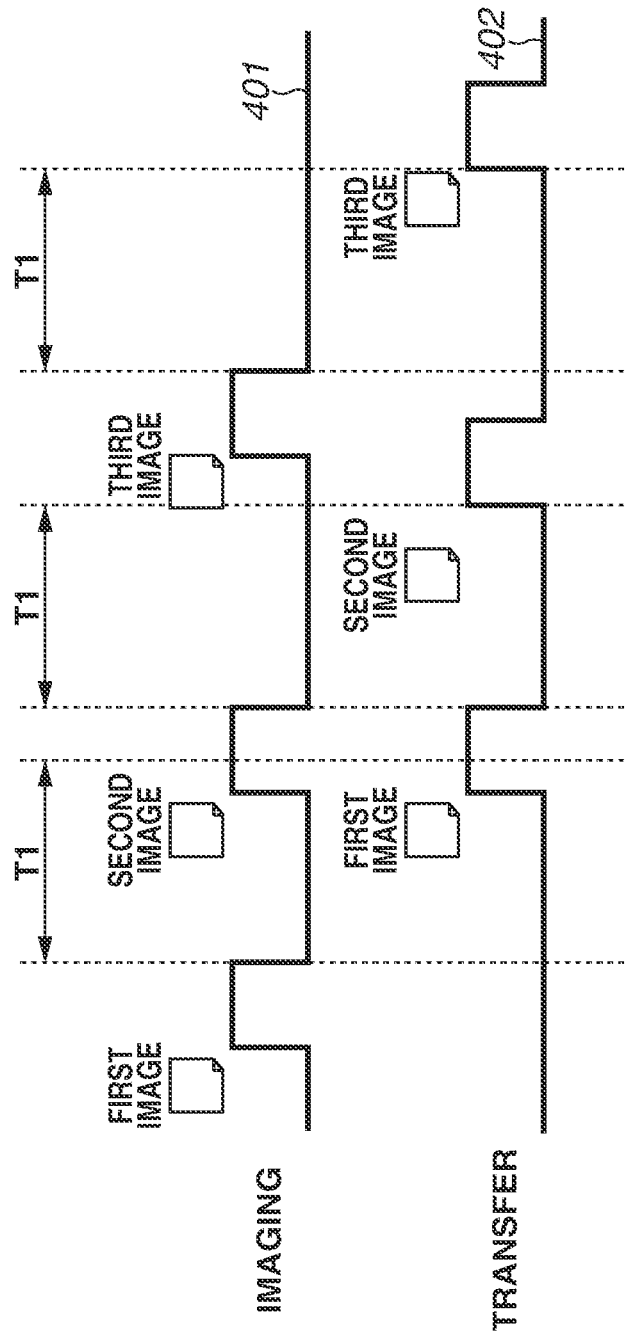

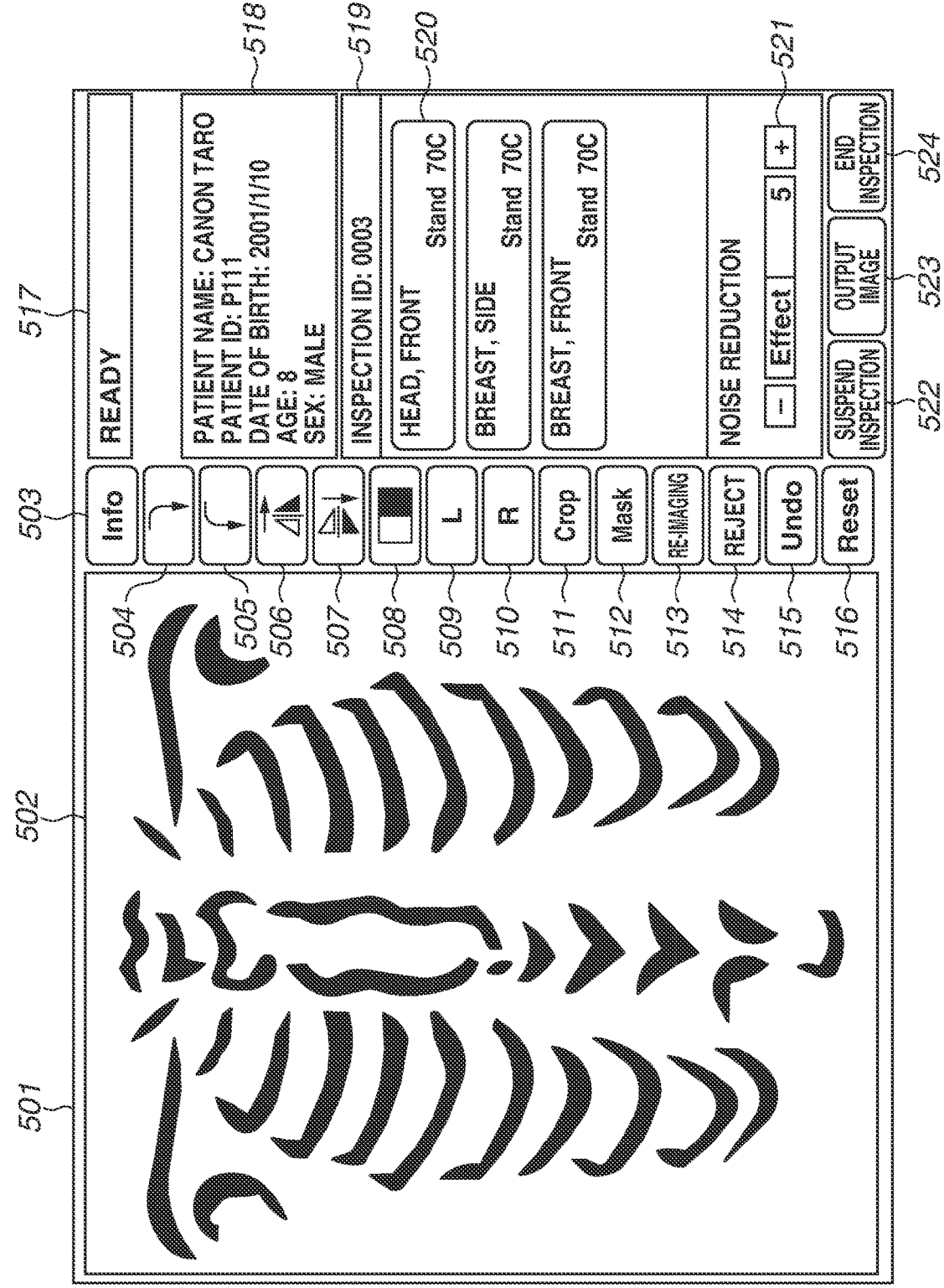

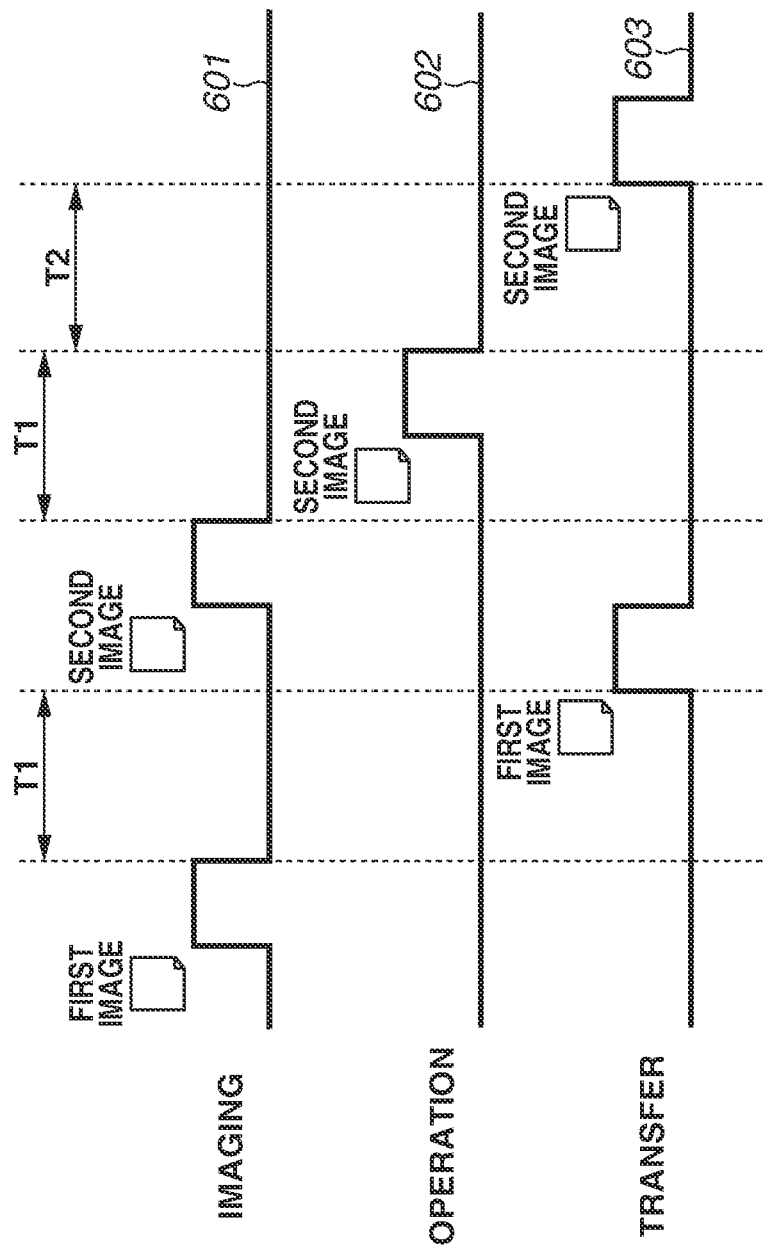

RADIATION IMAGING APPARATUS, TRANSFER CONTROL METHOD, AND STORAGE MEDIUM

BACKGROUND

Field

The present disclosure relates to a radiation imaging apparatus, a transfer control method, and a storage medium.

Description of the Related Art

X-ray sensors that convert an X-ray signal into a digital image and output the digital image, such as a flat panel detector, have become prevalent in recent years. Images collected by an X-ray imaging apparatus using such a sensor are transferred to an external picture archiving and communication system (PACS) and checked by doctors or technicians (see Japanese Patent Application Laid-Open No. 2002-140687).

In an inspection such as stomach fluoroscopy, a plurality of images can be collected. If all the images are transferred from the X-ray imaging apparatus to an external apparatus after completion of the inspection, the images are unable to be immediately checked in an interpretation room. A method for transferring an image from an X-ray imaging apparatus to an external apparatus immediately after imaging has thus been discussed. However, such a transfer method has the problem that if a captured image does have sufficient image quality, an operator is not able to adjust the image quality and the captured image is transferred with the image quality unadjusted. In view of this, Japanese Patent Application Laid-Open No. 2013-34621 discusses a technique that simplifies operations for transferring captured images to an external apparatus. The technique includes transferring X-ray images obtained by past X-ray imaging to the external apparatus a predetermined number of times based on acquisition of X-ray images.

SUMMARY

The present disclosure is directed to appropriately transferring captured images to an external apparatus without lowering operability.

According to an aspect of the present disclosure, a radiation imaging apparatus includes an acquisition unit configured to acquire a radiation image, and a transfer control unit configured to transfer the radiation image to a first external apparatus in the case where an elapsed time from a point in time when the radiation image is acquired exceeds a first time.

Further features will become apparent from the following description of exemplary embodiments with reference to the attached drawings.

BRIEF DESCRIPTION OF THE DRAWINGS

FIG. 4 is a diagram illustrating a timing chart of X-ray imaging and image transfer.

FIG. 5 is a diagram illustrating a display example of a graphical user interface (GUI).

FIG. 6 is a diagram illustrating a timing chart of X-ray imaging, operations, and image transfer.

DESCRIPTION OF THE EMBODIMENTS

Exemplary embodiments will be described below with reference to the drawings.

Figure 1:
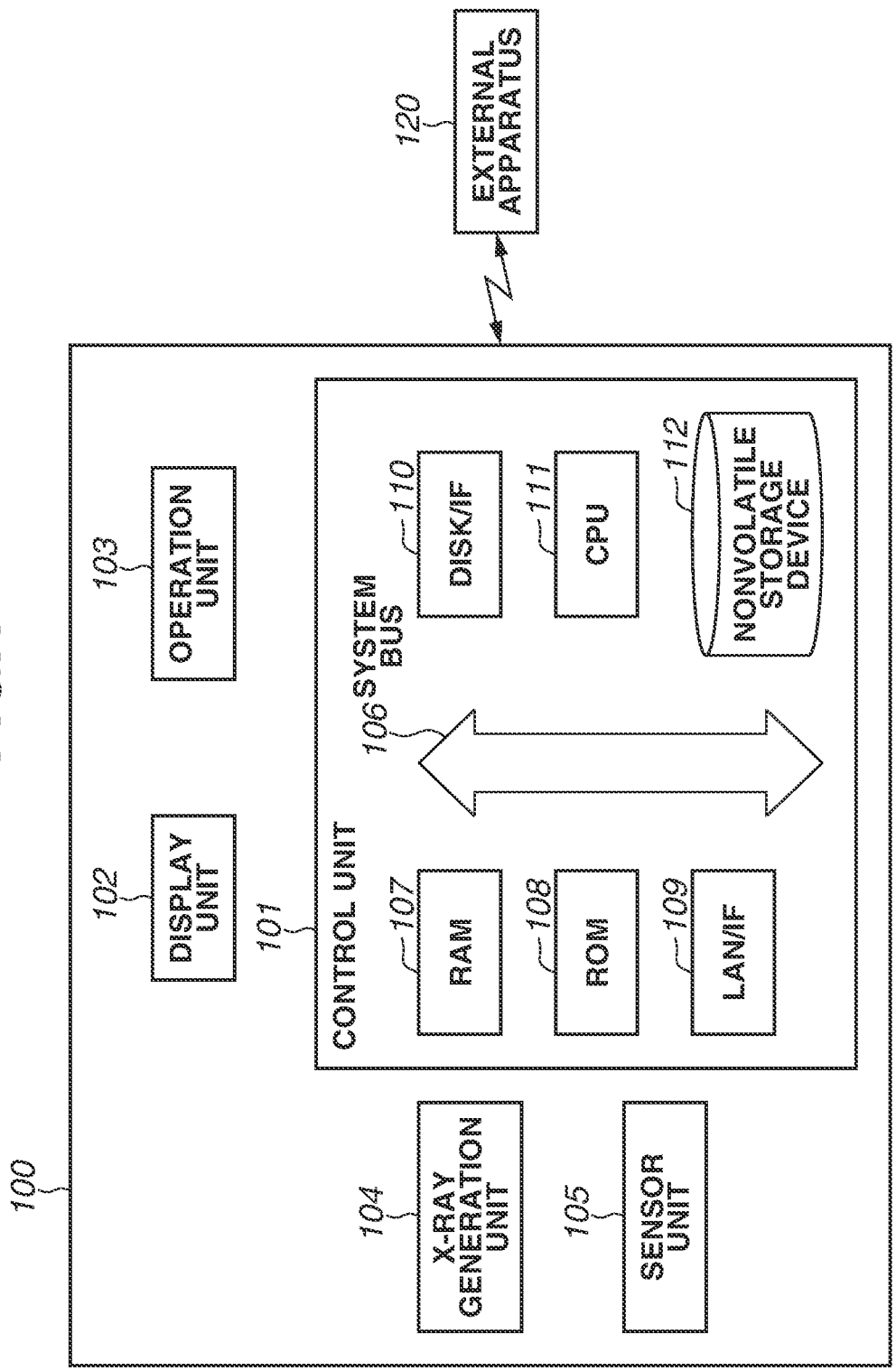
FIG. 1 is a diagram illustrating a hardware configuration of an X-ray imaging apparatus.

FIG. 1 is a diagram illustrating a hardware configuration of an X-ray imaging apparatus 100 according to a first exemplary embodiment. The X-ray imaging apparatus 100 is an example of a radiation imaging apparatus. A control unit 101 includes a random access memory (RAM) 107, a read-only memory (ROM) 108, a local area network interface (LAN/IF) 109, a disk interface (DISK/IF) 110, a central processing unit (CPU) 111, and a nonvolatile storage device 112 such as a hard disk. Such components are connected to each other by a system bus 106. A common general-purpose computer can be used as the control unit 101. The control unit 101 drives a sensor unit 105 and controls an X-ray generation unit 104 based on inputs made by an operator. The control unit 101 manages correction data, X-ray imaging conditions, and image data using a database. Functions and processing of the X-ray imaging apparatus 100, described below, are implemented by the CPU 111 reading a program stored in the ROM 108 or the nonvolatile storage device 112 and executing the read program.

An operation unit 103 includes input devices such as a mouse, a keyboard, and an irradiation switch. The operator uses the operation unit 103 to input various commands and data into the control unit 101. A display unit 102 includes a typical monitor such as a cathode-ray tube (CRT) display and a liquid crystal display. The display unit 102 displays image data and a graphical user interface (GUI) on the screen. The X-ray generation unit 104 includes an X-ray generation source, and emits X-rays based on instructions from the control unit 101. The sensor unit 105 is a sensor unit for imaging based on an X-ray signal transmitted through an object. The collected image is transferred to the control unit 101 and stored in the nonvolatile storage device 112. An external apparatus 120 is an external system for storing and displaying images transferred from the X-ray imaging apparatus 100. The external apparatus 120 is typically implemented as a picture archiving and communication system (PACS). The X-ray imaging apparatus 100 includes the control unit 101, the display unit 102, the operation unit 103, the X-ray generation unit 104, and the sensor unit 105, and controls X-ray imaging.

Figure 2:
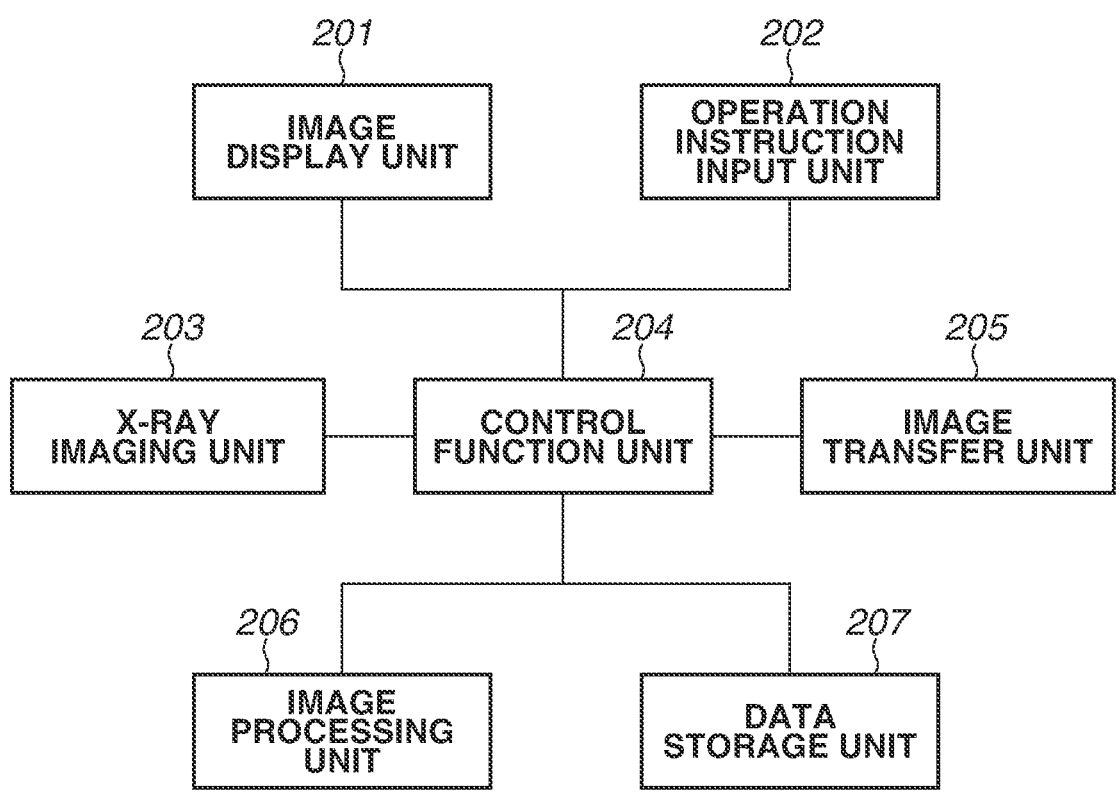
FIG. 2 is diagram illustrating a functional configuration of the X-ray imaging apparatus.

FIG. 2 is a diagram illustrating a functional configuration of the X-ray imaging apparatus 100. An image display unit 201 performs control to display captured images on the display unit 102 and to display a GUI for various operations. An operation instruction input unit 202 accepts various inputs associated with X-ray imaging via the operation unit 103. The operation instruction input unit 202 accepts input of patient information and inspection information using input devices such as the mouse and the keyboard of the operation unit 103, and accepts a start instruction for X-ray imaging using an input device such as a foot switch and a hand switch. An X-ray imaging unit 203 performs X-ray irradiation and collection of image data based on instructions from a control function unit 204 using the sensor unit 105 and the X-ray generation unit 104. The control function unit 204 has a function of performing control on the X-ray generation unit 104 and drive control on the sensor unit 105 in association with X-ray imaging, and control on image output to the external apparatus 120.

An image transfer unit 205 has a function of transferring image data to the external apparatus 120 based on instructions from the control function unit 204. An image processing unit 206 has functions for performing various types of image processing on captured image data. A data storage unit 207 stores image data collected by the X-ray imaging unit 203 into the nonvolatile storage device 112. The data storage unit 207 also has a function of storing and managing various types of data needed for X-ray imaging. Examples of such data include a threshold of a time from collection of image data to automatic transfer of the image data to the external apparatus 120, image processing parameters, and sensor calibration data.

Figure 3:
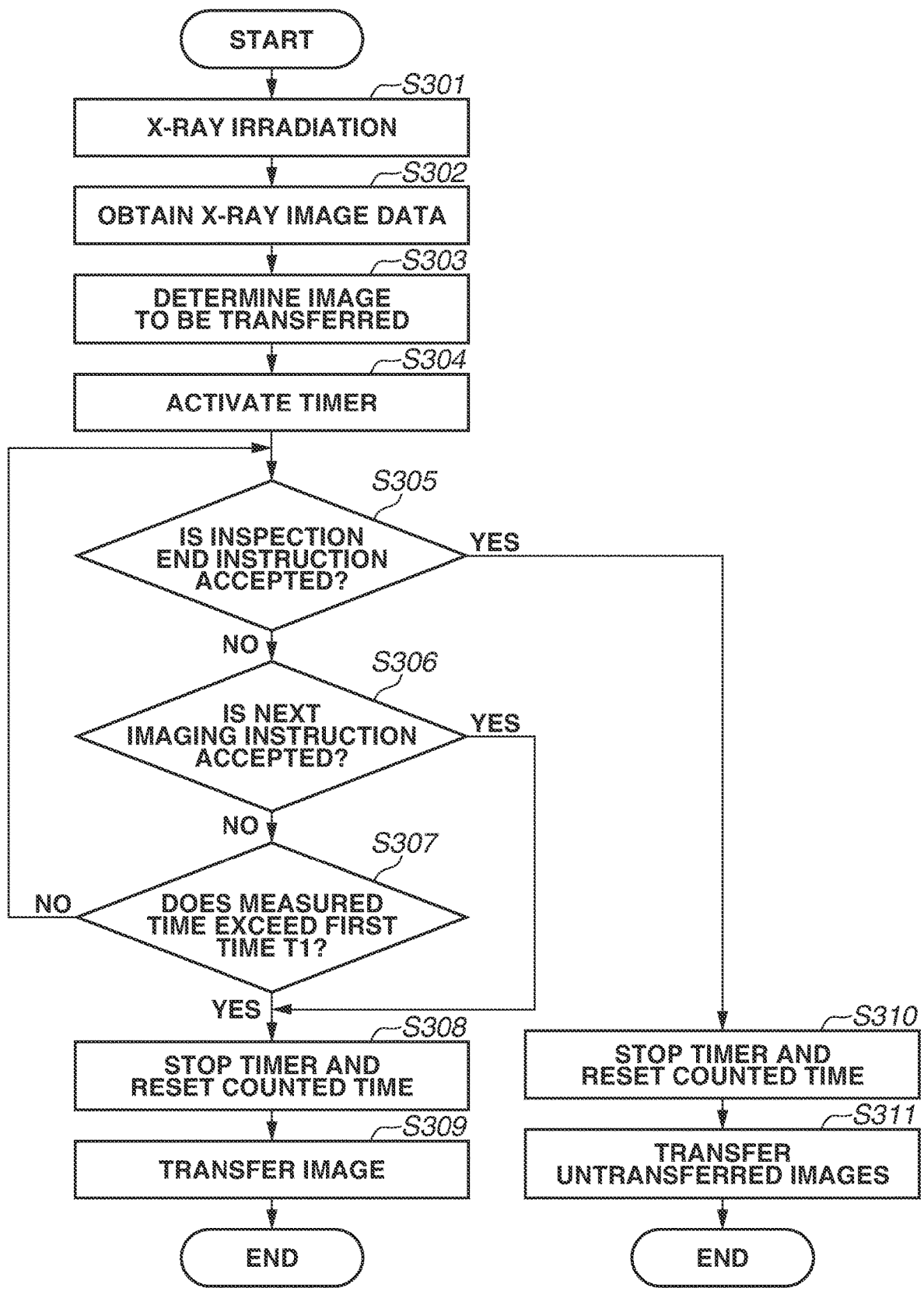
FIG. 3 is a flowchart illustrating transfer control processing.

FIG. 3 is a flowchart illustrating transfer control processing by the X-ray imaging apparatus 100. The operation instruction input unit 202 initially accepts an instruction to start an inspection via the operation unit 103. A period from when the operation instruction input unit 202 accepts an instruction to start an inspection to when the operation instruction input unit 202 accepts an instruction to end the inspection will be referred to as an inspection period. X-ray imaging is performed a plurality of times in one inspection period. Transfer processing is started by the operation instruction input unit 202 accepting the instruction to start an inspection.

In step S301, the control function unit 204 performs control to perform X-ray irradiation using the sensor unit 105 and the X-ray generation unit 104. As described above, this processing is typically performed based on a series of imaging start instructions including pressing of an inspection start button displayed on the GUI to start an inspection, selection of a needed imaging technique, and then pressing of an exposure button or a foot switch. In step S302, the control function unit 204 obtains X-ray image data (captured image) from the X-ray imaging unit 203. If the control function unit 204 obtains X-ray image data from the X-ray imaging unit 203, the data storage unit 207 stores the X-ray image data into the nonvolatile storage device 112. This processing is an example of processing for obtaining a radiation image.

In step S303, the control function unit 204 determines a transfer condition and determines an image to be transferred to the external apparatus 120. More specifically, the control function unit 204 determines the previously captured image in the same inspection period as the image to be transferred. If imaging is performed for the first time after a start of an inspection, there is no captured image obtained before. In such a case, no image is determined to be transferred in step S303. In step S304, the control function unit 204 activates a timer. The timer counts time.

In step S305, the control function unit 204 determines whether an inspection end instruction is accepted. The control function unit 204 accepts an inspection end instruction if an inspection end button 524 (FIG. 5) displayed on the GUI is pressed by the operator. If an inspection end instruction is accepted (YES in step S305), the processing proceeds to step S310. If an inspection end instruction is not accepted (NO in step S305), the processing proceeds to step S306.

In step S306, the control function unit 204 determines whether a next imaging instruction is accepted. If a next imaging instruction is accepted (YES in step S306), the processing proceeds to step S308. If a next imaging instruction is not accepted (NO in step S306), the processing proceeds to step S307. In step S307, the control function unit 204 determines whether the time measured by the timer exceeds a first time T1. The first time T1 is stored in the data storage unit 207 in advance. If the measured time exceeds the first time T1 (YES in step S307), the processing proceeds to step S308. If the measured time is less than or equal to the first time T1 (NO in step S307), the processing proceeds to step S305.

In step S308, the control function unit 204 stops the timer and resets the counted time. In step S309, the image transfer unit 205 transfers the captured image determined as the image to be transferred in step S303 to external apparatus 120. The transfer control processing then ends.

In step S310, the control function unit 204 stops the timer and resets the counted time. In step S311, the image transfer unit 205 transfers captured images that are not transferred at the point of processing to the external apparatus 120. The transfer control processing then ends. If an inspection end instruction is accepted, all captured images that remain untransferred are thus transferred to the external apparatus 120. This can prevent the captured images from being left untransferred in the X-ray imaging apparatus 100.

The first time T1 can be set and changed by user operations. If the first time T1 is set to a short time, an image can be immediately transferred to the external apparatus 120 after capturing the image. If the first time T1 is set to a long time, sufficient time for the operator to observe an image can be provided.

FIG. 4 is a diagram illustrating a timing chart of X-ray imaging and image transfer. X-ray imaging timing 401 illustrated in the upper row expresses how a total of three X-ray imaging operations are performed. Image transfer timing 402 illustrated in the lower row expresses how three transfer operations for transferring three captured images are performed. Suppose, as illustrated in FIG. 4, that an imaging instruction for a second image is accepted before the first time T1 elapses after the capturing of a first image. In such a case, the first image is transferred immediately after the capturing of the second image.

Suppose that after the capturing of the second image, an imaging instruction for a third image is not accepted before the first time T1 elapses. In such a case, the second image is transferred at the point in time when the elapsed time from the capturing of the second image exceeds the first time T1. If an imaging instruction for a fourth image is not accepted before the first time T1 elapses after the imaging of the third image, the third image is transferred at the point in time when the elapsed time from the capturing of the third image exceeds the first time T1.

The X-ray imaging apparatus 100 can edit an image based on user operations. FIG. 5 is a diagram illustrating a display example of a GUI for accepting user operations. A window 501 illustrated in FIG. 5 is a GUI screen displayed on the display unit 102 during inspection. The window 501 includes an image display area 502, in which a collected X-ray image is displayed. The X-ray image can be operated by various buttons. The buttons include an information button 503, a right rotation button 504, a left rotation button 505, a horizontal flip button 506, a vertical flip button 507, a white and black reversing button 508, an L mark arrangement button 509, and an R mark arrangement button 510. The buttons also include a crop setting button 511, a mask processing button 512, a re-imaging button 513, a rejection button 514, an undo button 515, and a reset button 516. The operator can edit the captured image by operating the foregoing buttons until the captured image is transferred to the external apparatus 120.

A status display section 517 is an area in which a status notified by the X-ray generation unit 104 or the sensor unit 105 is displayed in different colors and characters so that the operator can easily recognize the status. A patient information display area 518 displays information about the patient as subject of the inspection currently in progress. The patient information display area 518 displays a patient identification (ID), a patient name, sex, the date of birth, and other patient information. An inspection information display area 519 displays information about the inspection currently in progress. An imaging technique display area 520 displays imaging techniques included in the inspection in the form of a button or an icon. An image processing operation section 521 applies image processing to the displayed image. An inspection suspend button 522 provides an instruction to suspend the inspection currently in progress. An image output button 523 transfers an untransferred captured image. An inspection end button 524 provides an instruction to end the inspection currently in progress.

The rejection button 514 can be used to reject the displayed image and is used when imaging fails. If rejected images not needed for diagnosis are transferred to the external apparatus 120, the burden on the doctor who makes a diagnosis can increase. The control function unit 204 therefore excludes the captured image designated as a rejected image from the images to be transferred. If the timer has been started, the control function unit 204 performs control to stop the timer, reset the counted time, and not transfer the displayed image.

In another example, the image processing unit 206 can determine the quality of the captured image. If the image is determined to not be suitable for diagnosis, the control function unit 204 can exclude the image from those to be transferred as a rejected image. In such a case, the control function unit 204 does not start the timer in step S304.

Rejected images can be transferred to an external apparatus dedicated to rejected images to check the number of failed images from among all captured images, who repeatedly makes mistakes, and what kind of mistakes. In such a case, the control function unit 204 can transfer the rejected images to a transfer destination (external apparatus) different from that of the images other than the rejected images.

If the image output button 523 is operated, the control function unit 204 can transfer the captured image at that timing. The control function unit 204 can thereby transfer the captured image at the timing before automatic transfer by the transfer control processing.

As described above, according to the first exemplary embodiment, a captured image starts to be transferred after a lapse of a certain time from imaging. The operator therefore does not need to give a transfer instruction each time. If the image needs an adjustment, the user can make the adjustment to the image as needed since there is time before transfer. Image transfer can thus be implemented at an appropriate timing without the operator's operations to give transfer instructions. Since the number of operations by the operator is reduced, improved convenience to the operator and higher inspection throughput can be expected. Captured images can thus be appropriately transferred to the external apparatus without lowering operability.

Next, an X-ray imaging apparatus 100 according to a second exemplary embodiment will be described. The X-ray imaging apparatus 100 according to the second exemplary embodiment performs control, if a captured image is operated by the operator before transfer of the captured image, not to transfer an image captured until a second time T2 elapses from the timing of the operation. The time before the transfer of the captured image can thereby be sequentially extended according to operations. If a next imaging instruction is accepted before the lapse of the second time T2, the X-ray imaging apparatus 100 performs control to perform transfer immediately after capturing. The second time T2 is stored in a data storage unit 207 in advance. The second time T2 can be set and changed by user operations.

Examples of the foregoing operation include operations with respect to the right rotation button 504, the left rotation button 505, the horizontal flip button 506, the vertical flip button 507, and the white and black reversing button 508 described with reference to FIG. 5. Examples also include operations with respect to the L mark arrangement button 509, the R mark arrangement button 510, the crop setting button 511, the mask processing button 512, the re-imaging button 513, the rejection button 514, the undo button 515, and the reset button 516. The types of operations are not limited thereto.

FIG. 6 is a diagram illustrating a timing chart of X-ray imaging, operations, and image transfer. X-ray imaging timing 601 illustrated in the top row expresses how a total of two X-ray imaging operations are performed. Timing 602 illustrated in the middle row indicates a timing when an operation instruction is provided by the operator. Image transfer timing 603 illustrated in the bottom row expresses how transfer is performed twice to transfer two captured images.

Suppose, as illustrated in FIG. 6, that after a second image is captured, an operation on the second captured image is made before a first time T1 elapses. In such a case, an image transfer unit 205 performs control not to transfer the second captured image until the elapsed time from the point in time when the operation is made on the second captured image exceeds the second time T2. The image transfer unit 205 then starts to transfer the second captured image at the point in time when the elapsed time exceeds the second time T2. For example, if the operator adjusts an image processing parameter using a slider while observing the image, it can take a long time to finally complete the image processing adjustment. The X-ray imaging apparatus 100 according to the present exemplary embodiment sequentially extends the time before transfer, and can thus prevent an image on which the image processing adjustment is not completed from being transferred.

The second time T2 can be set to a relatively large value if the image processing adjustment takes long. The second time T2 can be set to a relative small value if the image processing adjustment does not take long. In such a manner, images can be transferred at an appropriate timing while preventing an image on which an image processing adjustment is not completed from being transferred.

In other respects than those described above, the configuration and processing of the X-ray imaging apparatus 100 according to the second exemplary embodiment are similar to those of the X-ray imaging apparatus 100 according to the first exemplary embodiment.

As a modification of the second exemplary embodiment, if an operation instruction from the operator is accepted, the control function unit 204 can reset the count of the timer instead of setting the second time T2. The control function unit 204 then performs control not to transfer the image until the first time T1 elapses from the point in time when the operation instruction is accepted. The control function unit 204 can then transfer the image at a timing when the first time T1 elapses from the point in time when the operation instruction is accepted.

The exemplary embodiments of the present disclosure have been described in detail above. However, the present disclosure is not limited to specific exemplary embodiments, and various changes and modifications can be made without departing from the essence of the present disclosure set forth in the claims.

Other Exemplary Embodiments

An exemplary embodiment of the present disclosure can be implemented by processing for supplying a program that implements one or more of the functions of the foregoing exemplary embodiments to a system or an apparatus via a network or a storage medium, and causing one or more processors of a computer of the system or apparatus to read and execute the program. An exemplary embodiment of the present disclosure can also be implemented by a circuit that implements one or more functions (for example, an application specific integrated circuit (ASIC)).

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MIIPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-007249, filed Jan. 19, 2018, which is hereby incorporated by reference herein in its entirety.

What is claimed is:

1. A radiation imaging apparatus comprising:
a data storage unit;
an acquisition unit configured to acquire a radiation image; and
a transfer control unit configured to transfer the radiation image to a first external apparatus in a case where an elapsed time from a point in time when the radiation image is acquired exceeds a first time that is stored in the data storage unit in advance,
wherein the transfer control unit is configured to, in a case where an operation on the radiation image is accepted at a point in time before the elapsed time from the point in time when the radiation image is obtained exceeds the first time, transfer the radiation image to the first external apparatus at a point in time when elapsed time from a point in time when the operation is accepted exceeds a second time that is stored in the data storage unit in advance.

2. The radiation imaging apparatus according to claim 1, wherein the transfer control unit is configured to perform control not to transfer the radiation image until the elapsed time from the point in time when the operation is accepted exceeds the second time.

3. The radiation imaging apparatus according to claim 1, wherein the transfer control unit is configured to, in a case where designation of rejection of the radiation image is accepted, perform control not to transfer the radiation image of which the designation of rejection is accepted.

4. The radiation imaging apparatus according to claim 1, wherein the transfer control unit is configured to, in a case where designation of rejection of the radiation image is accepted, perform control to transfer the radiation image of which the designation of rejection is accepted to a second external apparatus different from the first external apparatus.

5. The radiation imaging apparatus according to claim 1, further comprising a determination unit configured to determine whether the radiation image is a rejected image,
wherein the transfer control unit is configured to, in a case where the radiation image is determined as a rejected image, perform control not to transfer the radiation image determined as a rejected image.

6. A transfer control method performed by a radiation imaging apparatus, the transfer control method comprising:
acquiring a radiation image;
transferring the radiation image to a first external apparatus in a case where an elapsed time from a point in time when the radiation image is acquired exceeds a first time that is stored in a data storage unit in advance; and
transferring, in a case where an operation on the radiation image is accepted at a point in time before the elapsed time from the point in time when the radiation image is obtained exceeds the first time, the radiation image to the first external apparatus at a point in time when elapsed time from a point in time when the operation is accepted exceeds a second time that is stored in the data storage unit in advance.

7. A computer-readable storage medium storing a program for causing a computer to execute a transfer control method, the transfer control method comprising:
acquiring a radiation image;
transferring the radiation image to a first external apparatus in a case where an elapsed time from a point in time when the radiation image is acquired exceeds a first time that is stored in a data storage unit in advance; and
transferring, in a case where an operation on the radiation image is accepted at a point in time before the elapsed time from the point in time when the radiation image is obtained exceeds the first time, the radiation image to the first external apparatus at a point in time when elapsed time from a point in time when the operation is accepted exceeds a second time that is stored in the data storage unit in advance.

* * * * *